United States Patent [19]
Erekson et al.

[11] Patent Number: 4,950,830
[45] Date of Patent: Aug. 21, 1990

[54] DEHYDRATION OF ALIPHATIC AND ALICYCLIC HYDROCARBONS AND ALIPHATIC AND ALICYCLIC SUBSTITUTED AROMATIC HYDROCARBONS

[75] Inventors: Erek J. Erekson, LaGrange; Anthony L. Lee, Glen Ellyn, both of Ill.

[73] Assignee: Institute of Gas Technology, Chicago, Ill.

[21] Appl. No.: 274,499

[22] Filed: Nov. 21, 1988

Related U.S. Application Data

[63] Continuation-in-part of Ser. No. 172,808, Mar. 28, 1988, Pat. No. 4,826,796.

[51] Int. Cl.$^5$ .............................................. C07C 5/333
[52] U.S. Cl. .................................... 585/444; 585/624; 585/627; 585/661
[58] Field of Search ............... 585/443, 444, 624, 627, 585/650, 661

[56] References Cited

U.S. PATENT DOCUMENTS

| | | | |
|---|---|---|---|
| 3,830,853 | 8/1974 | Kheheian et al. | 585/444 |
| 3,849,292 | 11/1974 | Gleim | 585/500 |
| 4,499,324 | 2/1985 | Gaffney | 208/111 |
| 4,656,155 | 4/1987 | Josefowicz | 502/324 |

FOREIGN PATENT DOCUMENTS

| | | |
|---|---|---|
| 0112754 | 7/1984 | European Pat. Off. . |
| 0177327 | 4/1986 | European Pat. Off. . |
| 0183225 | 6/1986 | European Pat. Off. . |
| 2104462 | 4/1972 | France . |

OTHER PUBLICATIONS

Illingworth, G. F. and G. W. Lester, ACS Petroleum Division Preprints, 12, No. 3, 161, (1967).
Lee, K. W., M. J. Choi, S. B. Kim and C. S. Choi, Ind. Eng. Chem. Res., 26, 1951, (1987).
Kegeyan, E. M., I. S. Vardanyan and A. B. Nalbandyan, Kinetics and Catalysis, 17, No. 4,749,754 and No. 4,755,759, (1976).
Chemical Abstracts (USSR): 97:137153K, (1982); 99:70137t, (1983); 101:74734t, (1984); and 101:38205n, (1984).
Kirk-Othmer, Encyclopedia of Chemical Technology, Third Edition, vol. 21, Styrene, pp. 770-801.
Ward, D. J. et al., Hydrocarbon Processing, vol. 66, No. 3, Mar. 1987, pp. 47-48.
Fiedorow, R., W. Przystajko, J. Sopa and I. G. Dalla Lana, The Nature and Catalytic Influence of Cok on Alumina: Oxidative Dehydration of Ethylbenzene, Journal of Catalysis, 68, pp. 33-41, (1981).
Vrieland, G. E., Oxydehydration of Ethylbenzene to Styrene over Metal Phosphates, Journal of Catalysis, 111, pp. 1-13, (1988).

*Primary Examiner*—Asok Pal
*Attorney, Agent, or Firm*—Thomas W. Speckman

[57] ABSTRACT

A process for dehydrogenation of aliphatic and alicyclic hydrocarbon compounds and aliphatic and alicyclic substituted aromatic hydrocarbon compounds to form unsaturated aliphatic and alicyclic hydrocarbon chains. The catalyst is mixed basic metal oxide catalyst, one preferred catalyst is boron/alkali metal promoted metal oxide. Reaction of ethylbenzene according to this invention results in conversion to styrene.

35 Claims, No Drawings

DEHYDRATION OF ALIPHATIC AND ALICYCLIC HYDROCARBONS AND ALIPHATIC AND ALICYCLIC SUBSTITUTED AROMATIC HYDROCARBONS

CROSS-REFERENCE TO RELATED APPLICATION

This application is a continuation-in-part of copending U.S. Pat. Application Ser. No. 172,808, filed Mar. 28, 1988, now U.S. Pat. No. 4,826,796.

BACKGROUND OF THE INVENTION

1. Field of the Invention

This invention relates to a process using mixed basic metal oxide catalysts for production of unsaturated aliphatic and alicyclic chains by dehydrogenation of aliphatic and alicyclic hydrocarbon compounds and aliphatic and alicyclic substituted aromatic hydrocarbon compounds. One important dehydrogenation is the reaction of ethylbenzene in the presence of a mixed basic metal oxide catalyst according to this invention to produce styrene.

2. Description of the Prior Art

Borates and boron compounds have been used in partial oxidation of hydrocarbons, such as boric acid to oxidize long chain normal paraffins in the liquid phase (Illingworth, G.F. and G.W. Lester, ACS Petroleum Division Preprints, 12, No. 3, 161 (1967)) and oxidation of n-dodecane in the liquid phase to the corresponding alcohol (Lee, K.W., M.J. Choi, S.B. Kim and C.S. Choi, Ind. Eng. Chem. Res. 26, 1951 (1987)). Boric acid has been used by coating reactor walls in the combustion of methane to eliminate free radical destruction at temperatures of less than 513° C. (Kegeyan, E.M., I.S. Vardanyan and A.B. Nalbandyan, Kinetics and Catalysis 17, No. 4,749-754 and No. 4,755-759 (1976))

A number of publications describe oxidative methylation of toluene performed in Russia: Chemical Abstracts 97:127153 K (1982) teaches non-catalytic methylation of toluene depended mostly on pressure and PhMe/O/CH$_4$ molar ratio; Chemical Abstracts 99:70137t (1983) teaches oxidative methylation of toluene using a Ni—V oxide or V oxide catalyst; Chemical Abstracts 101:74734t (1984) teaches oxidative methylation of toluene in presence of 0 (max. 15 percent in reaction mixture) results in products including styrene; Chemical Abstracts 101:38205 n (1984) teaches simultaneous production of styrene, ethylbenzene, benzene, and phenols by reaction of toluene with C$_{1-4}$ alkanes in the presence of O and Fe$_2$O$_3$ or TiO$_2$ at 600° –800°. Productivity increased at higher pressure in presence of H$_2$O$_2$ and/or (Me$_3$C)$_2$O$_2$; and U.S. Pat. No. 3,830,853 teaches reaction of toluene with a lower paraffin hydrocarbon in the presence of oxygen at 600° –900° C. and space velocity of 2000–10000 hour$^{-1}$.

Styrene is an important commercial unsaturated aromatic monomer used extensively in the manufacture of plastics by polymerization and copolymerization. On a commercial scale, the great majority of the world's styrene is produced by dehydrogenation of ethylbenzene A review of styrene synthesis processes is given in Kirk-Othmer, Encyclopedia of Chemical Technology, Third Edition, Vol. 21, Styrene, pgs. 770-801.One commercial process for production of styrene is the UOP Styro-Plus process using ethylbenzene and superheated steam under vacuum for the catalytic dehydrogenation of ethylbenzene as taught by Ward, D.J. et al, Hydrocarbon Processing, Vol. 66, No. 3, March 1987, pgs 47–48. Use of coke-covered alumina and boron/alumina catalysts for oxidative dehydrogenation of ethylbenzene is taught by Fiedorow, R., W. Przystajko, M. Sopa and I.G. Dalla Lana, The Nature and Catalytic Influence of Coke on Alumina: Oxidative Dehydrogenation of Ethylbenzene, Journal of Catalysis 68, pgs. 33–41 (1981). Oxidative dehydrogenation of ethylbenzene to styrene over metal pyrophosphates, such as cerium, tin, zirconium, and titanium phosphates and calcium magnesium, strontium, barium, nickel, aluminum, thorium, zinc and silicon phosphates is taught by Vrieland, G.E., Oxydehydration of Ethylbenzene to Styrene over Metal Phosphates, Journal of Catalysis 111, pgs. 1–13 (1988). This article teaches the condensed phosphate surface is the dominant factor as a catalyst and that the cation has little or no effect.

SUMMARY OF THE INVENTION

The catalyst used in the process of this invention is described in our copending U.S. Pat. Application, Ser. No. 172,808. The catalyst and oxidative coupling of methane using the catalyst is fully described in U.S. Pat. Application Ser. No. 274,415, and oxidative coupling of aliphatic and alicyclic hydrocarbons with aliphatic and alicyclic substituted aromatic hydrocarbons using the same catalyst is fully described in U.S. Pat. Application Ser. No. 274,454. It is unexpected that catalysts active for oxidative coupling as described above involving carbon-carbon bond formation would also be active for dehydrogenation involving carbon-hydrogen bond breaking with subsequent carbon-carbon double bond formation. Dehydrogenation of saturated organics has been described by Thomas, Charles L, Catalytic Processes and Proven Catalysts, Chap. 6, Dehydrogenation, pgs. 41–45, Academic Press (1970).

This invention provides a catalytic process for dehydrogenation of aliphatic and alicyclic chains of aliphatic and alicyclic hydrocarbon compounds and aliphatic and alicyclic substituted aromatic hydrocarbon compounds to produce an unsaturation in the hydrocarbon chain. The reaction of an aliphatic or alicyclic hydrocarbon compound, an aliphatic or alicyclic substituted aromatic hydrocarbon compound and mixtures thereof in the dehydrogenation reaction is conducted in the presence of a mixed basic metal oxide catalyst at elevated temperature. The dehydrogenation may proceed directly according to the following general reaction of C—C bonding in a compound RH or R'CH$_3$ being converted to C=C bonding +H$_2$ or may proceed by oxidative dehydrogenation wherein C—C bonding in a compound RH or R'CH$_3$ + ½ O$_2$ is converted to C=C bonding +H$_2$O, wherein R is an aliphatic or alicyclic hydrocarbon radical having 2 and more carbon atoms; and R' is an aliphatic or alicyclic hydrocarbon radical substituted on an aromatic hydrocarbon ring. In the case of dehydrogenation of ethylbenzene to styrene according to this invention, direct dehydrogenation proceeds according to the general reaction:

and by partial oxidation or oxidative dehydrogenation according to the general reaction:

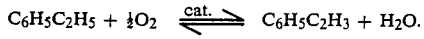

The mixed basic metal oxide catalyst used in the process of this invention has the formula:

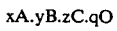

wherein
- A is an alkali metal selected from lithium, sodium, potassium, rubidium, cesium and mixtures thereof;
- B is a cation which has an ionization state 1 greater than the ionization state of C;
- B is selected from scandium, yttrium, lanthanum, actinium, aluminum, boron and mixtures thereof from Group IIIA and IIIB of the Periodic Table, preferably boron, aluminum, yttrium, and lanthanum when C is selected from beryllium, magnesium, calcium, strontium, barium, radium, zinc, cadmium, mercury and mixtures thereof from Group IIA and IIB of the Periodic Table, preferably magnesium, calcium, barium and zinc, and
- B is selected from titanium, zirconium, hafnium, silicon and mixtures thereof from Group IVA and IVB of the Periodic Table when C is selected from scandium, yttrium, lanthanum, actinium, aluminum, boron and mixtures thereof from Group IIIA and IIIB of the Periodic Table, preferably boron, aluminum, yttrium, and lanthanum;
- x and y are in the mole fractions of z such that when z=1 then x=0.001 to 0.25, preferably 0.05 to 0.15 and y=0.001 to 0.25, preferably 0.002 to 0.20; and
- q is a number necessary to maintain charge balance with 0 being oxygen.

In a preferred embodiment, a boron/alkali metal promoted metal oxide catalyst having boron in amounts of about 0.2 to about 20 mole percent (about 0.05 to about 5.0 weight percent), alkali metal promoter selected from the group consisting of lithium, sodium and potassium in amounts of about 0.1 to about 25 mole percent (about 0.1 to about 40 weight percent), metal oxide selected from the group consisting of magnesium oxide, calcium oxide, zinc oxide, and barium oxide are suitable for the catalytic dehydrogenation process according to this invention.

DESCRIPTION OF PREFERRED EMBODIMENTS

The process of this invention provides unsaturated aliphatic and alicyclic chains by dehydrogenation of saturated carbon atoms of an aliphatic or alicyclic hydrocarbon compound and an aliphatic or alicyclic substituted aromatic hydrocarbon and mixtures thereof in the presence of a mixed basic metal oxide catalyst, such as a boron/alkali metal promoted metal oxide catalyst.

Suitable aliphatic and alicyclic hydrocarbon compounds for use as feedstocks in the process of this invention include straight and branched chain saturated aliphatic hydrocarbons, such as ethane, propane, butane, heptane, pentane, hexane, octane, isobutane, isohexane, isooctane and mixtures thereof; cyclic chain saturated alicyclic hydrocarbons, such as cyclobutane, cycloheptane, cyclohexane and mixtures thereof. Suitable aliphatic and alicyclic substituted aromatic hydrocarbon compounds for use as feedstocks in this invention are aromatic ring hydrocarbons having at least one saturated aliphatic or alicyclic hydrocarbon radical substituent on the aromatic ring, such as ethylbenzene, indan, tetralin and mixtures thereof.

The reactant is fed to the reaction zone in contact with the above defined catalyst at a space velocity of about 500 to about 50,000, preferably about 1000 to about 5000 vol/vol/hr for direct dehydrogenation and for oxidative dehydrogenation. For oxidative dehydrogenation oxygen may be added up to a mole amount of about 5 moles oxygen per mole hydrocarbon, preferably about 0.5 to about 2.0 moles oxygen per mole hydrocarbon. Steam may be added in an amount of up to about 1 mole of steam per mole hydrocarbon to inhibit undesired side reactions when oxygen is used in the feed for oxidative dehydrogenation. Steam does not enter into the reaction but solely acts as an oxidation inhibitor. For direct dehydrogenation, without oxygen in the feed, steam may be used as a heat carrying agent and up to 10 moles of steam per mole of hydrocarbon may be required.

Any oxygen containing gas not containing interfering chemical compounds is useful as a feedstock in this invention. The term "oxygen containing gas" as used throughout this disclosure and claims, refers to gas containing oxygen, such as air and gases having an oxygen content of up to 100 percent. It is preferred to use oxygen containing gas comprising over 50 volume percent oxygen. The amounts of oxygen used in the process of this invention is expressed as pure oxygen. The oxygen containing gas may be preheated by thermal exchange with the catalyst bed to a temperature suitable for the reaction controlling step of the process.

The catalyst used in the catalytic process for dehydrogenation according to this invention is a mixed basic metal oxide catalyst having the formula $xA.yB.zC.qO$ wherein A, B, C, x, y, z and q have the meanings set forth above with 0 being oxygen. The catalysts used in the process of this invention have only one oxidation state besides the metal, that is Ti, Zr, Hf and Si are only +4 and B, Al, Y and La are only +3, while Mg, Ca, Sr and Ba are only +2 and Li, K, Na, Rb and Cs are only +1. In a particularly preferred embodiment, the catalyst of this invention is a boron/alkali metal promoted metal oxide catalyst having boron in amounts of about 0.2 to about 20 mole percent (about 0.05 to about 5 weight percent) and preferably about 0.4 to about 2 mole percent (about 0.1 to about 0.5 weight percent); alkali metal promoter selected from the group consisting of lithium, sodium and potassium in amounts of about 0.1 to about 25 mole percent (about 0.1 to about 40 weight percent) and preferably about 0.5 to about 8 mole percent (about 0.5 to about 2.0 weight percent) and the remainder metal oxide selected from the group consisting of magnesium oxide, calcium oxide, zinc oxide, and barium oxide. A preferred catalyst is boron/lithium promoted magnesium oxide having about 0.20 to about 0.30 weight percent boron and about 0.8 to about 1.2 weight percent lithium.

The catalyst for use in this invention may be prepared by mixing water soluble ions and/or compounds of elements set forth as alkali metal (A) and cation (B) to obtain complete solution of the solids. A wide variety of non-interfering ions may be used to form suitable water soluble compounds as long as they do not cause undesired chemical interference. Suitable such compounds include acids, oxides, hydrides, and nitrates, carbonates, hydroxides, respectively. The aqueous solution of (A) and (B) are added to metal oxide (C) powder and well mixed followed by drying at a sufficient temperature and for a sufficient time to expel volatile components. The mixture is then crushed and sieved to a small size for catalytic use. Conventional and well known catalyst manufacturing techniques may be employed to produce the catalyst material noted above. When preparing these catalytic materials, it is preferred to employ manufacturing techniques resulting in a product having a substantially uniform or homogeneous composition. Shaping of the material may be effected according to conventional techniques of the art, particularly tableting, or pelleting or extrusion. The catalyst may be used unsupported or alternatively it may be supported on an inert support as known to the art, such as alumina, silica, activated carbon and the like.

A preferred catalyst may be prepared by mixing a water soluble compound of boron, such as boric acid, boron oxides, borohydrides, and a water soluble salt of the alkali metal promoter, such as nitrate, carbonate, hydroxide or water soluble ion to obtain complete solution of the solids. The aqueous solution of boron and alkali metal is added to the metal oxide powder with stirring to obtain a homogeneous mixture which may then be dried at a temperature in excess of about 110° C. The dried mixture may then be calcined at a temperature of 700° to 750° C. for a sufficient time to expel volatile portions. The mixture is then crushed and sieved to an appropriately small mesh size of about $-6$ to about $+40$, preferably about $-12$ to about $+20$ for use as a catalyst.

The catalyst may be placed into a reactor, such as a tube-shell fixed bed, fluidized bed, moving bed, or interbed heat exchange type, Fischer-Tropsch type, or other reactor type known to the art. The dehydrogenation process according to this invention is carried out by passing the gaseous aliphatic or alicyclic hydrocarbon or aromatic feedstock over the mixed basic metal oxide catalyst as defined above at a space velocity of about 500 to about 50,000 vol/vol/hr providing gas residence times of about 0.002 to about 0.00002 hour preferably about 0.0002 to about 0.00007 hour. Suitable temperatures are about 200° to about 1000° C., preferably about 600° to about 850° C. for direct dehydrogenation and preferably about 450° to about 700° C. for oxidative dehydrogenation. The reaction may be carried out at pressures of about 1 psia to about 1515 psia, preferably about 1 psia to about 25 psia for direct dehydrogenation and preferably about 1 psia to about 150 psia for oxidative dehydrogenation. Pressures above atmospheric may enhance the rate of reaction. Suitable reactor vessels for use at the above operating temperatures and pressures are well known to the art. The products of the single reactor used in the process of this invention may be passed to a simple separator for separation of the hydrocarbon product, condensate, and vent gas.

One important dehydrogenation reaction according to the process of this invention is the production of styrene directly by dehydrogenation of ethylbenzene or by oxidative dehydrogenation of ethylbenzene in the presence of the above defined catalyst according to the reactions set forth above. At 727° C. the heat of reaction (H) for oxidative dehydrogenation is $-29.4$ kcal/mole exothermic and the sensible heat plus the heat of vaporization of ethylbenzene is about 33.0 kcal/mole. Thus the oxidative dehydrogenation process operates close to autothermal conditions after initial light-off. Conventional processes for production of styrene from ethylbenzene feedstock require large amounts of superheated steam (800° C. and molar ratio 14 steam to 1 ethylbenzene) because the conversion of ethylbenzene to styrene is endothermic. The process of this invention uses a single reactor in a process that does not require superheated steam.

The specific examples are intended to be illustrative only and are not intended to limit the invention in any way.

EXAMPLE I

A mixture of 3.07 grams Fisher Certified lithium nitrate and 0.43 gram Aesar 99.99 percent pure boric acid was added to a beaker. Deionized water, 50ml, was added to the beaker and stirred to obtain complete solution of the solids in the water. The aqueous solution of lithium nitrate and boric acid was slowly added to 30.0 grams alpha magnesium oxide powder and stirred to obtain a homogeneous preparation which was then dried overnight at 118° C. The composition of the mixture was 1.0 weight percent elemental lithium and 0.24 weight percent elemental boron. The mixture was then calcined for 15 minutes at 700° C. and crushed and sieved to $-12+20$ mesh. Chemical analysis after calcining showed 0.97 weight percent elemental lithium and 0.17 weight percent elemental boron. Surface area of the product was 2.0 meters$^2$/gram. The product was then used as a catalyst in accordance with Example X following which analysis showed 0.94 weight percent lithium, 0.20 weight percent boron, and surface area of 1.5 meters$^2$/gram.

EXAMPLE II

In a manner similar to Example I an aluminum/lithium promoted magnesium oxide catalyst was formed by adding 3.08 grams of Fisher Certified lithium nitrate and 2.63 grams of Fisher Certified aluminum nitrate to a beaker. Deionized water, 50 ml, was added to the beaker and stirred to obtain complete solution of the solids in the water. The aqueous solution of lithium nitrate and aluminum nitrate was slowly added to 30.0 grams of alpha magnesium oxide powder and stirred to obtain a homogeneous preparation which was then dried overnight at 118° C. The composition of the mixture was 1.0 weight percent elemental lithium and 0.6 weight percent elemental aluminum. The mixture was then calcined for 15 minutes at 700° C. and crushed and sieved to $-12+20$ mesh.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for producing unsaturated aliphatic and alicyclic hydrocarbon chains by dehydrogenation, said process comprising:

dehydrogenating a compound selected from aliphatic hydrocarbon compounds, alicyclic hydrocarbon compounds, aliphatic substituted aromatic hydrocarbon compounds, alicyclic substituted aromatic hydrocarbon compounds, and mixtures thereof in the presence of a mixed basic metal oxide catalyst having the formula:

$xA.yB.zC.qO$ wherein

A is an alkali metal selected from lithium, sodium, potassium, rubidium, cesium and mixtures thereof;

B is a cation which has an ionization state greater than the ionization state of C;

B is selected from the group consisting of scandium, yttrium, lanthanum, actinium, aluminum, boron and mixtures thereof when C is selected from the group consisting of beryllium, magnesium, calcium, strontium, barium, radium, zinc, cadmium, mercury and mixtures thereof, and B is selected from the group consisting of titanium, zirconium, hafnium, silicon and mixtures thereof, when C is selected from the group consisting of scandium, yttrium, lanthanum, actinium, aluminum, boron and mixtures thereof;

x and y are in mole fractions of z such that when $z=1$ then x-0.001 to 0.25, and $y=0.001$ to 0.25; and q is a number necessary to maintain charge balance with 0 being oxygen.

2. A process according to claim 1 wherein said aliphatic and alicyclic hydrocarbon compounds are selected from straight and branched chain saturated aliphatic hydrocarbons, cyclic chain saturated alicyclic hydrocarbons, aromatic ring hydrocarbons having at least one saturated aliphatic substituent on said aromatic ring, aromatic ring hydrocarbons having at least one saturated alicyclic substituent on said aromatic ring, and mixtures thereof.

3. A process according to claim 2 wherein said aliphatic hydrocarbon compounds are selected from ethane, propane, butane, heptane, pentane, hexane, octane, isobutane, isohexane, isooctane, and mixtures thereof.

4. A process according to claim 2 wherein said alicyclic hydrocarbon compounds are selected from cyclobutane, cycloheptane, cyclohexane, and mixtures thereof.

5. A process according to claim 2 wherein said aromatic hydrocarbon compounds are selected from ethylbenzene, indan, tetralin and mixtures thereof.

6. A process according to claim 1 wherein B is selected from the group consisting of boron, aluminum, yttrium, lanthanum and mixtures thereof and C is selected from the group consisting of magnesium, calcium, barium, zinc and mixtures thereof.

7. A process according to claim 6 wherein $x=0.05$ to 0.15 and $y=0.002$ to 0.20.

8. A process according to claim 1 wherein B is selected from the group consisting of silicon, titanium, zirconium, hafnium and mixtures thereof and C is selected from the group consisting of boron, aluminum, yttrium, lanthanum and mixtures thereof 9. A process according to claim 8 wherein x-0.05 to 0.15 and $y=0.002$ to 0.20.

10. A process according to claim 1 wherein said catalyst is a boron/alkali metal promoted metal oxide, said boron present in about 0.2 to about 20 mole percent, said alkali metal selected from the group consisting of lithium, sodium and potassium and present in about 0.1 to about 25 mole percent, and the balance said metal oxide selected from the group consisting of magnesium oxide, calcium oxide, zinc oxide, barium oxide and mixtures thereof.

11. A process according to claim 10 wherein said boron is present in about 0.4 to about 2 mole percent.

12. A process according to claim 10 wherein said alkali metal is present in about 0.5 to about 8 mole percent.

13. A process according to claim 10 wherein said alkali metal is selected from the group consisting of lithium, sodium, potassium and mixtures thereof.

14. A process according to claim 10 wherein said alkali metal is lithium.

15. A process according to claim 10 wherein said metal oxide is selected from the group consisting of magnesium oxide, calcium oxide, zinc oxide, barium oxide and mixtures thereof.

16. A process according to claim 10 wherein said metal oxide is magnesium oxide.

17. A process according to claim 10 wherein the gas residence time is about 0.002 to about 0.00002 hr.

18. A process according to claim 10 wherein the gas residence time is about 0.0005 to about 0.0001 hr.

19. A process according to claim 10 wherein said process is carried out at a temperature of about 200° to about 1000° C.

20. A process according to claim 10 wherein said dehydrogenation is direct dehydrogenation in the absence of oxygen and said process is carried out at a temperature of about 600° to about 850° C.

21. A process according to claim 10 wherein said dehydrogenation is oxidative dehydrogenation in the presence of up to 5 moles oxygen per mole said hydrocarbon compound.

22. A process according to claim 10 wherein said process is carried out at a pressure of about 1 to about 1515 psia.

23. A process according to claim 10 wherein said dehydrogenation is direct dehydrogenation in the absence of oxygen and said process is carried out at a temperature of about 600° to about 850° C. and said process is carried out at a pressure of about 1 to about 25 psia.

24. A process according to claim 10 wherein said dehydrogenation is oxidative dehydrogenation in the presence of up to 5 moles oxygen per mole said hydrocarbon compound and said process is carried out at a pressure of about 1 to about 150 psia.

25. A process according to claim 1 wherein the gas residence time is about 0.002 to about 0.00002 hr.

26. A process according to claim 1. wherein the gas residence time is about 0.0005 to about 0.0001 hr.

27. A process according to claim 1 wherein said process is carried out at a temperature of about 200° to about 1000° C.

28. A process according to claim 1 wherein said dehydrogenation is direct dehydrogenation in the absence of oxygen and said process is carried out at a temperature of about 600° to about 850° C.

29. A process according to claim 1 wherein said dehydrogenation is oxidative dehydrogenation in the presence of up to 5 moles oxygen per mole said hydrocarbon compound.

30. A process according to claim 1 wherein said process is carried out at a pressure of about 1 to about 1515 psia.

31. A process according to claim 1 wherein said dehydrogenation is direct dehydrogenation in the absence of oxygen and said process is carried out at a temperature of about 600° to about 850° C. and said process is carried out at a pressure of about 1 to about 25 psia.

32. A process according to claim 1 wherein said dehydrogenation is oxidative dehydrogenation in the presence of up to 5 moles oxygen per mole said hydrocarbon compound and said process is carried out at a pressure of about 1 to about 150 psia.

33. A process for producing unsaturated aliphatic and alicyclic hydrocarbon chains by dehydrogenation, said process comprising:

directly dehydrogenating in the absence of oxygen a compound selected from aliphatic hydrocarbon compounds, alicyclic hydrocarbon compounds, aliphatic substituted aromatic hydrocarbon compounds, alicyclic substituted aromatic hydrocarbon compounds, and mixtures thereof in the presence of a mixed basic metal oxide catalyst having the formula:

$$xA.yB.zC.qO$$

wherein
- A is an alkali metal selected from lithium, sodium, potassium, rubidium, cesium and mixtures thereof;
- B is a cation which has an ionization state 1 greater than the ionization state of C;
- B is selected from the group consisting of scandium, yttrium, lanthanum, actinium, aluminum, boron and mixtures thereof when C is selected from the group consisting of beryllium, magnesium, calcium, strontium, barium, radium, zinc, cadmium, mercury and mixtures thereof, and
- B is selected from the group consisting of titanium, zirconium, hafnium, silicon and mixtures thereof, when C is selected from the group consisting of scandium, yttrium, lanthanum, actinium, aluminum, boron and mixtures thereof;
- x and y are in mole fractions of z such that when $z=1$ then x-0.001 to 0.25, and y=0.001 to 0.25; and
- q is a number necessary to maintain charge balance with 0 being oxygen.

34. A process for producing unsaturated aliphatic and alicyclic hydrocarbon chains by dehydrogenation, said process comprising:

oxidatively dehydrogenating in the presence of up to 5 moles oxygen per mole hydrocarbon a compound selected from aliphatic hydrocarbon compounds, alicyclic hydrocarbon compounds, aliphatic substituted aromatic hydrocarbon compounds, alicyclic substituted aromatic hydrocarbon compounds, and mixtures thereof in the presence of a mixed basic metal oxide catalyst having the formula:

$$xA.yB.zC.qO$$

wherein
- A is an alkali metal selected from lithium, sodium, potassium, rubidium, cesium and mixtures thereof;
- B is a cation which has an ionization state 1 greater than the ionization state of C;
- B is selected from the group consisting of scandium, yttrium, lanthanum, actinium, aluminum, boron and mixtures thereof when C is selected from the group consisting of beryllium, magnesium, calcium, strontium, barium, radium, zinc, cadmium, mercury and mixtures thereof, and
- B is selected from the group consisting of titanium, zirconium, hafnium, silicon and mixtures thereof, when C is selected from the group consisting of scandium, yttrium, lanthanum, actinium, aluminum, boron and mixtures thereof;
- x and y are in mole fractions of z such that when $z=1$ then x-0.001 to 0.25, and y=0.001 to 0.25; and
- q is a number necessary to maintain charge balance with 0 being oxygen.

35. A process according to claim 34 wherein about 0.5 to about 2.0 moles oxygen per mole hydrocarbon is used.

* * * * *